US006833061B1

(12) United States Patent
Fuhr et al.

(10) Patent No.: US 6,833,061 B1
(45) Date of Patent: Dec. 21, 2004

(54) METHODS FOR ISOELECTRIC PARTICLE SEPARATION

(75) Inventors: Günter Fuhr, Berlin (DE); Jonas Korlach, Berlin (DE); Rudolf Ehwald, Berlin (DE)

(73) Assignee: Evotec Technologies GmbH, Duesseldorf (DE)

( * ) Notice: Subject to any disclaimer, the term of this patent is extended or adjusted under 35 U.S.C. 154(b) by 0 days.

(21) Appl. No.: 09/147,951

(22) PCT Filed: Sep. 26, 1997

(86) PCT No.: PCT/EP97/05295

§ 371 (c)(1),
(2), (4) Date: May 24, 1999

(87) PCT Pub. No.: WO98/13689

PCT Pub. Date: Apr. 2, 1998

(30) Foreign Application Priority Data

Sep. 28, 1996 (DE) .......................................... 196 40 076
Jun. 9, 1997 (DE) .......................................... 197 24 266

(51) Int. Cl.$^7$ ........................ G01N 27/26; G01N 27/447
(52) U.S. Cl. ........................ 204/548; 204/450; 204/459; 204/600; 204/610; 204/644
(58) Field of Search ................................ 204/450, 601, 204/600, 610, 459, 548, 644

(56) References Cited

U.S. PATENT DOCUMENTS 5,114,555 A * 5/1992 Stimpson ................ 204/610 X

FOREIGN PATENT DOCUMENTS

| EP | 0 617 048 A1 | 9/1994 |
| GB | 2118975 A | * 11/1983 |
| WO | WO 98/13689 | * 4/1998 |

OTHER PUBLICATIONS

E. N. Lightfoot et al. *Separation Science and Technology*, vol. 16, No. 6, pp. 619–656 (1981).
R.A.M. Osher et al. in "The Dynamics of Electrophoresis" Editor B.J. Radola VCH, Weinheim, 1992, pp. 163–231.
Foret, Frantisek et al. "Capillary Electrophoresis" in "Advances in Electrophoresis," Editor VCH–Verlagsgesellschaft mbH, 1989, vol. 3, pp. 273–347.
K.D. Caldwell et al. in "Science," vol. 176, pp. 296–298.
L.F. Kesner et la. in "Analytical Chemistry," vol. 48, 1976, pp. 1834–1839.
E. N. Lightfoot et al. *Electropolarization Chromatography*, vol. 16, pp. 619–656 (1981).

* cited by examiner

Primary Examiner—Nam Nguyen
Assistant Examiner—John S. Starsiak, Jr.
(74) Attorney, Agent, or Firm—Birch, Stewart, Kolasch & Birch, LLP

(57) ABSTRACT

In order to isoelectrically separate particles with a pH-dependent net charge, the particles are exposed in a guiding liquid to electric field forces. The pH value of the guiding liquid is set in such a way that at least one predetermined type of particle is separated from the remaining particles and migrates to a fixing collecting means under the effect of the electric field forces. The collecting means is for example a porous hollow fiber delimited by electrodes which generate the electric field forces and crossed by the guiding liquid together with the sample to be separated. The particles whose isoelectric point matches the pH value of the guiding liquid run unimpeded through the fibers, whereas the remaining particles are pressed against the inner wall of the fiber and are prevented from being carried away with the liquid flow.

3 Claims, 8 Drawing Sheets

METHODS FOR ISOELECTRIC PARTICLE SEPARATION

Figure 1:
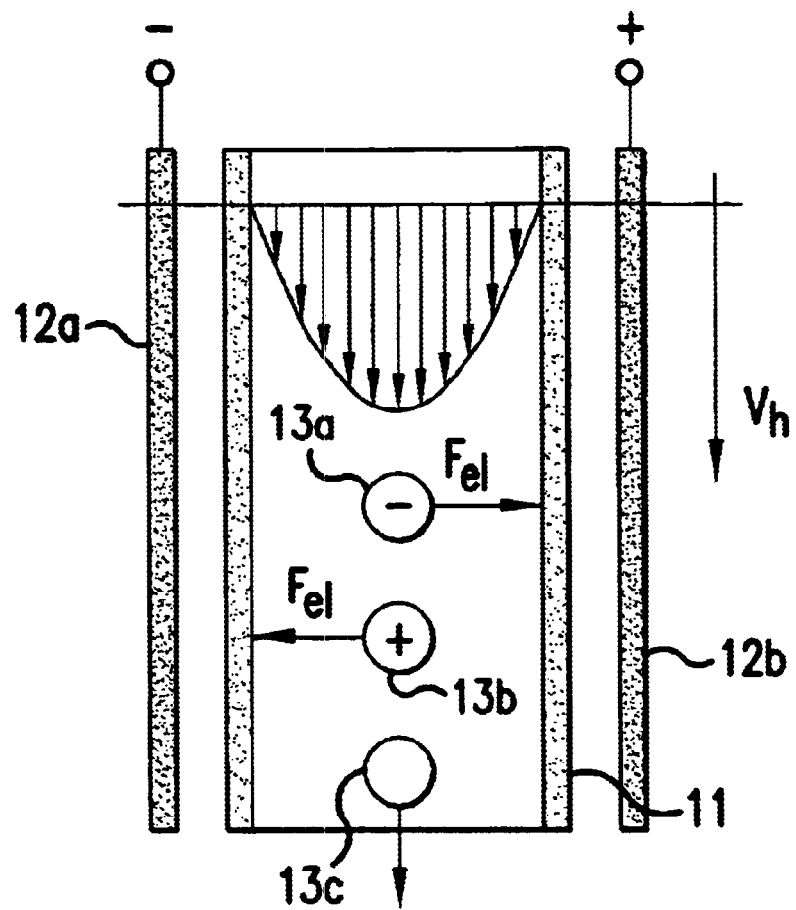

This application is the national phase under 35 U.S.C. §371 of prior PCT International Application No. PCT/EP97/05295 which has an International filing date of Sep. 26, 1997 which designated the United States of America.

The invention concerns methods and devices for isoelectric separation of particles whose charge characteristics depend on the pH value of a guiding fluid, especially for separating ampholytic suspended particles, colloids or biological cells. The invention concerns in particular the separation of such particles from a guiding fluid flow.

Numerous separation techniques are known from molecular biology; biochemistry, medicine and biotechnology whose function is based on charge differences of molecules within a substance that is to be separated. In the case of amphoteric ion compounds (socalled ampholytes or ampholytic molecules), the molecular charge depends on the pH value of the surrounding solution. The isoelectric point (hereafter referred to as the IP) of a compound is the pH value at which the net charge of the amphoteric molecules equals zero. The charge of the molecule is positive for a pH value smaller than the IP and negative in the opposite case.

In isoelectric focusing (hereafter referred to as IEF), proteins with different IPs are separated by making use of spatial pH gradients along a separation length (see R. A. M. Osher et al. in "The Dynamics of Electrophoresis", published by B. J. Radola, VCH, Weinheim, 1992, pp 163–231). IEF is performed, for example, using porous gel matrices or, for analytical separation of the smallest samples, using thin capillaries as what is called cIEF (see F. Foret et al. "Capillary Electrophoresis" in "Advances in Electrophoresis", vol. III, published by A. Chrambach et al., VCH, Weinheim, pp 273–347).

For the following reasons conventional IEF presents disadvantages and its use is restricted. Retrieval of the separated substances from a carrier material, especially for further processing like analysis, medication applications or the like, calls for elaborate procedures by which the separated substances themselves may be modified, or which lead to substance losses. The necessary use of additional substances to form a pH gradient that is as wide and linear as possible produces restrictions in terms of further use of the separated samples. The socalled carrier ampholytes used as additional substances are, in chemical terms, a highly diverse substance mix that is difficult to separate from the separated protein fractions. Furthermore, cIEF is restricted to minimal sample quantities that cannot be collected separately and are not separable from the carrier ampholytes.

The problem when socalled IPG membranes are used to form the pH gradient is that proteins, because of the necessity of passing through such a membrane, must pass through a milieu whose ionic concentration is very low. Consequently, sensitive proteins can denaturize or precipitate in this region. For this reason the strictest requirements are made in IEF for uniformity of the voltage gradients in the separation length. Finally, problems can occur in IEF in the form of electroosmosis in extreme pH ranges, the carrier medium (gel) heating up and altering (destruction of the gel) for instance.

To overcome such drawbacks, systems were developed in which ampholyte separation is produced by the effect of an external electric field and without modifying additional substances. One separating system is known, for example, that works by the method of socalled electric field flow fractionating (eFFF) (see K. D. Caldwell et al. in "Science", vol. 176, 1972, pp 296–298). In this separating system a continuous fluid stream is conducted through a narrow duct between two ion flow permeable membranes, into which the sample to be separated is injected as a narrow band. External electrodes, in electrical contact with the duct through a surrounding fluid, produce different degrees of retardation, as a function of charge, of the protein molecules in the fluid stream. However, use of this method is restricted to protein molecules with IPs that are relatively far apart. Furthermore, no complete protein separation could be achieved. Control of the pH value of the fluid stream—and thus of the molecular charge state—is not a facet of this familiar separating system.

The eFFF system is not applicable in practice. Although the samples could be separated (incompletely), collection of the separated fractions was not implemented. Furthermore, the times for separation are unacceptably high. A follow-on development of the above mentioned eFFF system (see L. F. Kesner et al. in "Analytical Chemistry", vol. 48, 1976, pp 1834–1839) produced analysis or separation times of several hours even on a laboratory scale for example.

A modified eFFF system described by Lightfoot et al. (see "Separation Science and Technology", vol. 16, 1981, pp 619–656) makes use off cylindrical duct geometry. The separation performance of this system was also unacceptable in practical terms. Furthermore, protein retardation showed itself to be a complex function of a large number of parameters, eg the buffer ions that were used, the sample quantity, the sort of protein and properties of the duct wall. Nor is this familiar system intended for pH control or, say, separation of proteins with different IPs.

There is pronounced interest in substance separation for the production of high-purity substances, beyond the sphere of the laboratory, on an industrial scale. Because of the restrictions and disadvantages mentioned however, no continuous substance separation is known to date, using the named systems, that produces adequate separation performance and speed for the practical sphere.

The object of the invention is to indicate improved methods of isoelectric particle separation distinguished, in particular, by higher separation speed, greater reliability, and a broader range of application in terms of separable particles and the surrounding solutions. The object of the invention is also to indicate corresponding, continuous isoelectric purification methods. The object of the invention also consists in providing devices for implementing the methods of particle separation and further application possibilities.

The named objects are achieved by methods for isoelectric particle separation in which particles with a net charge or charge density that is a function of the pH value of the surroundings are exposed to electric field forces in a guiding fluid passing by collection means, whereby the pH value of the guiding fluid is set so that, through the effect of the electric field forces, at least one predetermined particle type undergoes a change in motion as a function of charge and is moved to the collection means, intended for soluble fixing of the charged particles or by devices for isolectric particle separation that include: electrode means for forming an electric field in a guiding fluid with particles whose net electric charge or charge density is a function of the pH value of the guiding fluid; pH setting means being adapted to set the pH value of the guiding fluid so that at least one predetermined particle type of the particles in the guiding fluid undergoes a change in motion as a function of charge through the effect of the electric field; and collection means arranged between the electrode means and the guiding fluid for soluble fixing of charged particles. Preferred embodiments of the invention are disclosed hereinafter.

The separation technique according to the invention is based on the idea of controlling or setting the pH value in a guiding fluid in which the particles to be separated are exposed to electric field forces so that all particle types with a net charge go through a motion dependent on charge, and the remaining, for the most part neutral particles show no change in their state of motion, whereby the particles moving as a function of charge are moved to collection means (collection device). The particles are retained at least temporarily on the collection means. This involves fixing on the surface or in the volume of the collection means. The duration of fixing is determined by the separation conditions, especially modulation with time of the electric field forces, alteration of the pH value, the structure of the collection means and/or relative motion between the collection means and the guiding fluid.

A major difference from the eFFF technique described above is thus that the particles are not differently retarded as a function of charge but that, through control of the pH value in the guiding fluid, a condition is created that defines what type of particle, exposed to the effect of an external electric field, moves into an at least temporarily fixed state and is possibly released again. To distinguish it from the eFFF technique, isoelectric separation according to the invention is therefore named pH-controlled electroretention chromatography. The collection means are effective as real restrain means. Thus a method is proposed for inverse isoelectric particle separation in which particles with a charge dependent on pH value are passed by collection means in a guiding fluid and the pH value of the guiding fluid is set or modified so that only the uncharged particles remain in the guiding fluid, while the charged particles are moved through an electric field to the collection means and are consequently fixed, at least temporarily, as a function of pH value.

The induced change of motion of the predetermined type of particle, according to the invention, is directed to the collection means so that the predetermined type of particle that is to be separated arranges itself or collects on or behind the collection means. The collection means are formed of a collection arrangement, for example, between electrode means to generate the external electric field and the guiding fluid. It is possible to move the collection means in relation to the guiding fluid.

The collection arrangement is preferably semi-permeable as a function of substance. Semi-permeability can mean, for instance, that the collection arrangement is permeable for the molecules of the guiding fluid or for ions dissolved in the guiding fluid, but impermeable, ie a barrier effect, for the substance or type of particle to be separated. Semi-permeability can also be implemented so that some of the type of particle to be separated with smaller particle sizes are let through, and the remainder of the particles to be separated with larger particle sizes are not let through. The collection arrangement is preferably a delimitation of the guiding fluid from the particles to be separated. Outside of the collection arrangement, in a surrounding solution with adjustable pH value, are the electrode means for forming the electric field.

The invention can be implemented with a static or a flowing guiding fluid. In both cases the collection arrangement forms a compartment or a vessel with at least one opening for entry or exit of the sample to be separated.

The separating effect is especially good and fast if the displacement path of the particles from the location of the sample in the guiding fluid (possibly flowing tangentially to the adjoining collection means) to the collection means is kept as small as possible. Preferably the collection arrangement will have characteristic dimensions that are in the flow direction of the guiding fluid much greater than the displacement path. The displacement path or inner dimensions of the compartments are of the order of mm or smaller for example.

In one preferred embodiment, the collection arrangement is formed of at least one longish, hollow element (eg tubular) that has semi-permeable or porous walls and through which the guiding fluid flows with the particle sample to be separated. Other forms of collection arrangement are also possible, especially with a rectangular instead of a round cross-section. In one particularly advantageous and preferred implementation the collection arrangement consists of at least one straight or bent hollow fiber with, at least in part, semi-permeable walls.

Isoelectric separation according to the invention can be implemented with ampholytic molecules or all other synthetic or biological particles (especially cells or viruses) that exhibit electrical characteristics like those of ampholytic molecules, in particular a net charge or charge density that is a pH function of the surroundings.

Optionally, in order to purify the guiding fluid, particles that are to be removed from the guiding fluid may be moved out of the guiding fluid by the collection means. The flow velocity of the guiding fluid may be reduced or dropped to zero at least temporarily when the particles to be separated are exposed to the electric field forces. A sample with the particles to be separated and/or the guiding fluid may be fed through microducts in the porous wall. The pH value of a sample solution, with which the particles are introduced to the guiding fluid, of the guiding fluid and/or of the surrounding solution may be set independently so that predetermined pH gradients form on the collection means. The pH value of a sample solution, in which the particles to be separated are introduced to the guiding fluid, and/or of the guiding fluid may be set by diffusive exchange processes with the surrounding solution.

Depending on the application, the purpose of isoelectric separation according to the invention can be aimed at obtaining the predetermined particle type that undergoes a change of motion in the electric field as a function of charge, or the remaining particles without change of the state of motion.

A device for isoelectric particle separation according to the invention contains electrode means for forming an electric field in a guiding fluid with the particles that are to be separated, and means for controlling or setting the pH value in the guiding fluid. There are also collection means between the electrode means and the guiding fluid that, in addition to a collecting function for a type of particle that is to be separated, also have a delimiting function from a surrounding solution with adjustable pH value. The collection means are permeable at least for ions dissolved in the surrounding solution and the guiding fluid, so that the pH value of the guiding fluid can also be set and controlled by setting the pH value of the surrounding solution.

Preferred forms of application of the invention are all separation processes on sample mixes that contain at least one particle type with ampholytic characteristics, and/or investigations of certain substances for determining the isoelectric point, of titration curves or aggregation response. The device according to the invention can also be used to reduce the ionic concentration of the guiding fluid in the field of pH-controlled electrodialysis.

The present invention provides also a device for isolectric particle separation that includes: electrode means for forming an electric field in a guiding fluid with particles whose net electric charge or charge density is a function of the pH value of the guiding fluid; pH setting means being adapted to set the pH value of the guiding fluid so that at least one predetermined particle type of the particles in the guiding fluid undergoes a change in motion as a function of charge through the effect of the electric field; and collection means arranged between the electrode means and the guiding fluid for soluble fixing of charged particles.

Isoelectric particle separation according to the invention possesses the following advantages:

Fractionating or separation occurs without additional substances, in particular without carrier ampholytes or other means such as for generating a pH gradient for instance. Since no pH gradient is generated, this simplifies considerably a preparative procedure in the flow-through system or collection of the required (possibly even all) separated fractions. The separated or purified fractions are available for further manipulation after separation, without having changed from the original form. The separated fractions are, in particular, always in the same solution with the same, possibly slightly reduced or even higher concentration. The system according to the invention can be used and automated for both discontinuous and continuous separation of particles as a function of their IPs. Both spatial fractionation and, by variation of the pH value during the separation process, fractionation as a function of time is possible. The speed of separation is high, of the order of minutes, as will be exemplified in what follows. The separation system allows configuration of the electrode means within tight confines so that, compared to conventional separation processes, sufficiently high field strength can be produced with relatively small voltages. This minimizes the energy consumption of systems according to the invention and relaxes conditions for samples sensitive to temperature.

Another aspect of the present invention is the use of a device for separation of at least one particle type from the guiding fluid to obtain a purified fraction of the separated particles and/or a purified guiding fluid, determining electrical and thermodynamic characteristics of substances like isoelectric point, titration curves or aggregation response, boosting the concentration of a particle solution or suspension, or reducing the ionic concentration of the guiding fluid.

Further features and advantages of the invention will emerge from the following description of implementations referring to the attached drawings.

FIG. 1: Schematic explaining the forces that appear in separation according to the invention, FIG. 2: Curve illustrating protein separation according to the invention, FIG. 3: Curve illustrating further protein separation according to the invention, FIG. 4: Curve of a model calculation illustrating the selectivity that can be achieved with the invention, FIG. 5: Curve illustrating further protein separation according to the invention, FIG. 6: Schematic of a separation device according to the invention, FIGS. 7, 8, 9: Schematics of modified hollow fiber arrangements, FIG. 10: Schematics of combined separating and concentrating device, FIG. 11: Schematic of multi-compartment system according to the invention, and FIG. 12: Schematic of modified implementation of a separation device according to the invention.

The following explanation refers, by way of example, to an implementation of the invention in which the collection means are formed of a hollow fiber. But the principles explained can be implemented in the same way in other geometries of the collection means. Furthermore, the invention is not restricted to protein separation as used here as an example, it can be implemented for any particles with ampholytic characteristics.

In one implementation of the invention (see below for details, FIG. 6), a thin hollow fiber passes through a reaction cavity containing the surrounding solution, at least two electrodes and means for pH setting. The electrodes are designed for application of a pedetermined DC voltage. The walls of the hollow fiber are provided with a large number of pores of defined size to create semi-permeability. The size of the pores is chosen so that the solution (eg water) and ions transporting the electric current are let through, but the molecules to be separated are usable to pass through the wall. The hollow fiber can for example, have an inner diameter (or clear width or socalled lumen) in the range of millimeters to micrometers. The means for pH setting are provided to control or set the pH value of the surrounding solution by what is a familiar, conventional procedures eg electrically or by titration.

The sample to be separated is conducted through the lumen of the hollow fiber with a second fluid, the guiding fluid. The guiding fluid will preferably have the same pH value or the same ion composition as the surrounding solution. For this purpose the guiding fluid can be extracted from the reaction cavity for example. Alternatively it is possible for the guiding fluid to have a different pH value. At the upstream end of the hollow fiber there are means for introducing the sample to be separated into the guiding fluid, and at the downstream end there are means of detection and/or collection. The forces appearing during separation according to the invention will now be explained with reference to FIG. 1.

FIG. 1 is a schematic section of a portion of a hollow fiber 11 through which the guiding fluid with a certain pH value flows and the sample 13a, 13b and 13c that is to be separated. The hollow fiber 11 is arranged between two DC electrodes 12a, 12b so that the guiding fluid with the sample passes through an electric field.

According to the pH value of the guiding fluid, the sample comprises negatively charged molecules 13a, positively charged molecules 13b and uncharged molecules 13. Exposed to the effect of the electric field forces, the charged molecules move to the edge of the guiding fluid. At the edge of the fluid flow, ie on the hollow fiber acting as the collection means, the charged molecules are prevented from being transported further with the guiding fluid and thus locally fixed. Local fixing can generally be achieved by a sufficiently strong electric field that has one component perpendicular to the direction of flow of the guiding fluid ($V_h$) and by an adhering (eg rough or porous) inner surface of the hollow fiber. In a preferred implementation of the invention the geometry of the hollow fiber and the flow velocity of the guiding fluid are selected so that the flow profile illustrated in FIG. 1 assumes what an essentially parabolic shape. Such a flow profile is characterized by the fact that flow velocity is highest in the middle of the guiding fluid, ie in the center of the hollow fiber, reducing towards the edges. Such a flow profile is produced, for example, when generating a laminar guiding fluid flow through the hollow fiber. Flow velocity is zero in the immediate vicinity of the hollow fiber wall. In this case the molecules are excluded entirely from further transport in the guiding fluid flow (electroretention).

A molecule whose IP matches the pH value of the guiding fluid possesses no net electric charge and consequently is unaffected by the electric field. Thus, as a function of the pH value, a certain type of molecule is conducted through the hollow fiber to a detector or collector, for example, while the charged particles on the hollow fiber wall are retained.

Figure 2:
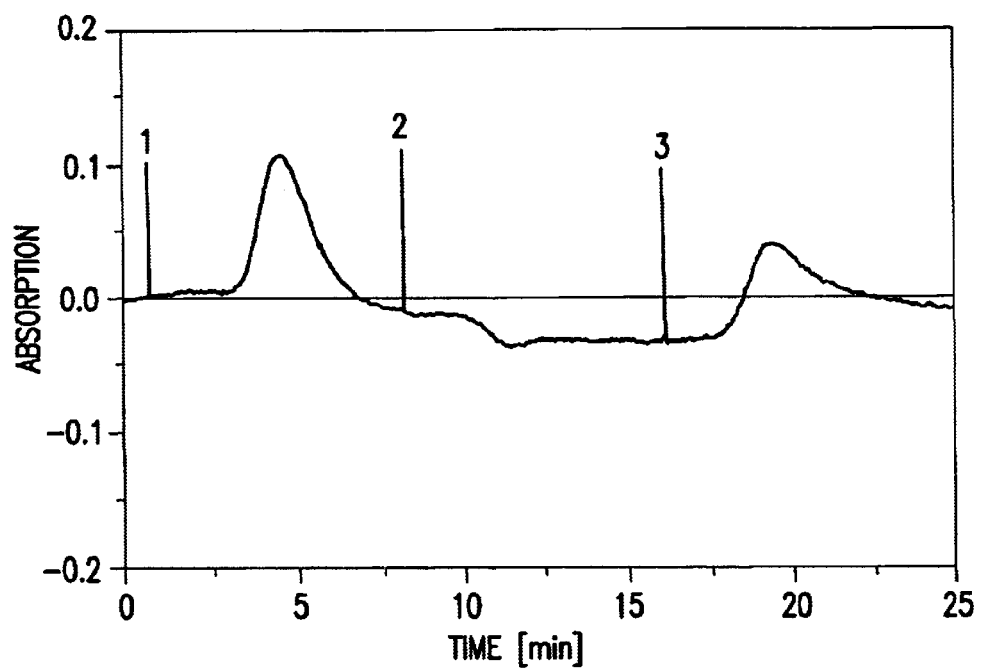
Figure 3:
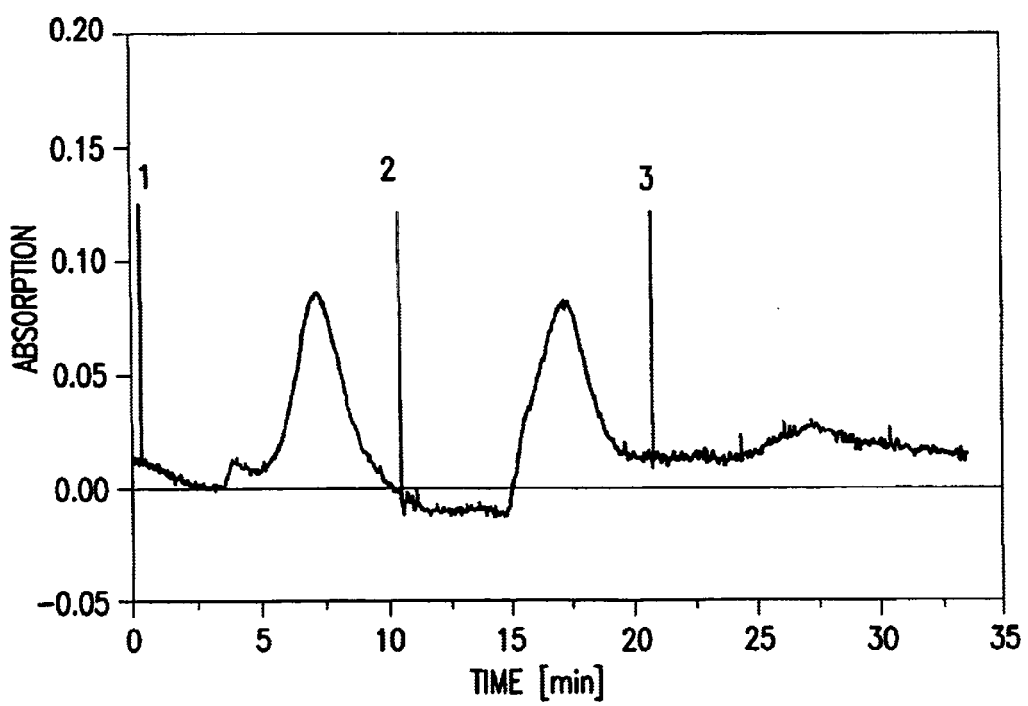

FIG. 2 and FIG. 3 show experimental results for protein separation. The curves are absorption values recorded by a detector as a function of time at the downstream end of the hollow fiber. At point 1 in FIG. 2 a defined amount of protein is introduced to the guiding fluid and detected without the effect of an electric field as a function of time (max. 5 min). At point 2 an amount of protein is again introduced to the guiding fluid, but this time with the effect of an electric field. There is no change in absorption—or at least only a slight negative one produced by the measuring system—because the protein is retained. The retained protein does not enter the carrier flow again, and is thus detected (max. 20 min), until the electric field is removed.

FIG. 3 shows an experiment where the protein has an IP that corresponds to the pH value of the surrounding solution or guiding fluid however. Between points 1 and 2 (without the influence of a field) and 2 and 3 (with the influence of a field) it can now be seen that the protein remains unaffected because of the absence of a net charge and reaches the detector unaltered. When the field is removed (point 3), no absorption of the protein is detected but instead only the impurities contained in the starting sample. This shows the purifying effect produced by passing the protein through the electric field, in the course of which the impurities were withdrawn from the sample.

In addition to the separation of proteins with an IP that differs from the pH value according to FIG. 2, or the separation of impurities according to FIG. 3, the following variants are possible of the methods according to the invention.

It is possible to alter the pH value of the surrounding solution and thus of the guiding fluid with time. If variation with time is attuned to the length of the hollow fiber or the flow velocity of the guiding fluid, it is possible, under the continuous influence of a field and by varying the pH value, to separate components from the sample with a time offset, ie in the order of their IPs. Controlled, carrier-free pH variation can be produced over a wide range with accuracy of approx. 0.1 to 0.01 pH units with one pH state. In this timed fractionating the pH value is thus increased or reduced as a function of time in such a way that the pH value corresponds to the IP of a component of the sample for a certain time interval. The time interval is selected so that there will be complete separation of the particular component from the sample and spatial separation on the inner wall of the hollow fiber from the next component (fractionating of a substance mix).

In addition to pH variation for charge variation of the molecules or particles, it is possible to provide, instead of the above mentioned DC voltage between the electrodes, modulation of the electric field in time and/or space. The result is again an optimization in separation of the sample.

Another alternative is variation of the hydrodynamic flow through the hollow fiber (variation of flow velocity). In this way it is possible to restrict the flow of the guiding fluid with time or to halt it while the sample is exposed to the effect of the field in the hollow fiber element.

One variation of a separating or purifying process according to the invention is possible when a semi-permeability of the hollow fiber (choice of pore size) is created so that at least part of the released molecules that are to be separated are allowed to pass. A pH value is set in the surrounding solution of the guiding fluid that corresponds to the IP of the component to be isolated. After injection of the sample as a narrow band or in continuous application, all components whose IP does not correspond to the set pH value are shifted out of the hollow fiber lumen through the pores of the wall into the surrounding solution. The component, now purified, remaining the hollow fiber can be collected with the guiding fluid stream after the isolating gap. The concentration of the purified component only decreases slightly because of diffusion through the wall of the hollow fiber, but it can be increased again by a follow-up concentration booster (see FIG. 10).

Figure 4:
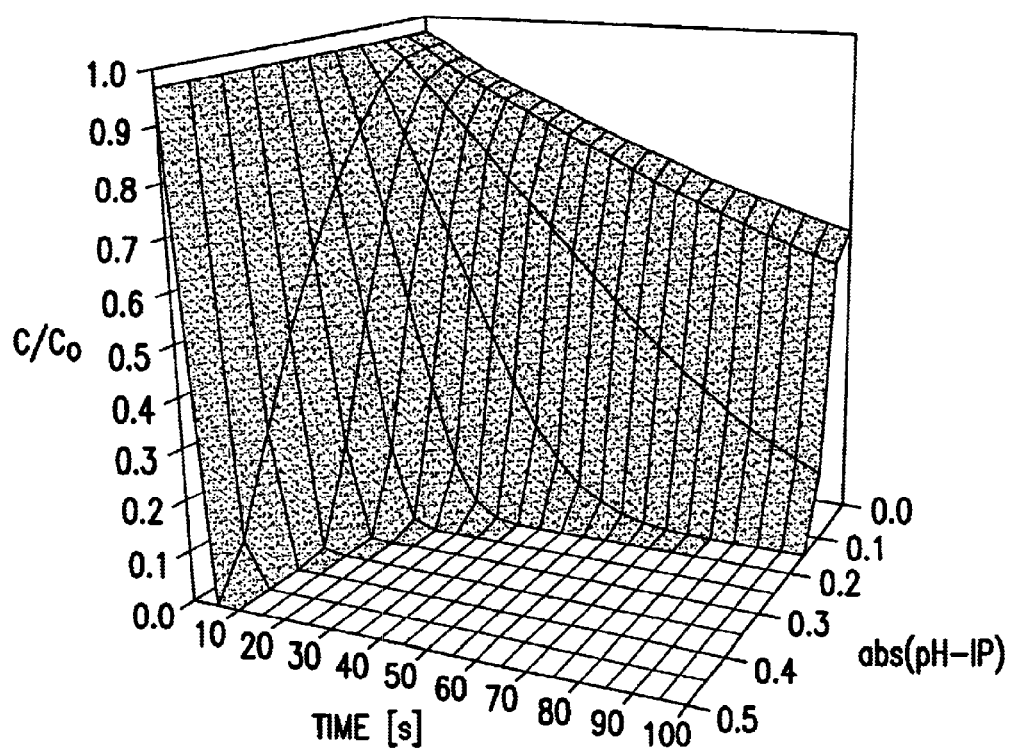

FIG. 4 shows the result of a model calculation to illustrate the effect of the electric field on molecules whose IP does not correspond to the pH value of the guiding fluid. The parameters of the graphic representation are time, relative concentration change $C/C_o$ and absolute deviation (abs (pH-IP)) between the IP,and the pH value. It can be seen that, even with slight deviations of the IP from the pH value, the concentration of the particular component fast reduces to zero because of the strong effect of the electric field.

In the continuous method the surrounding solution enriching itself with the separated components is simultaneously replaced by fresh surrounding solution.

Figure 5:
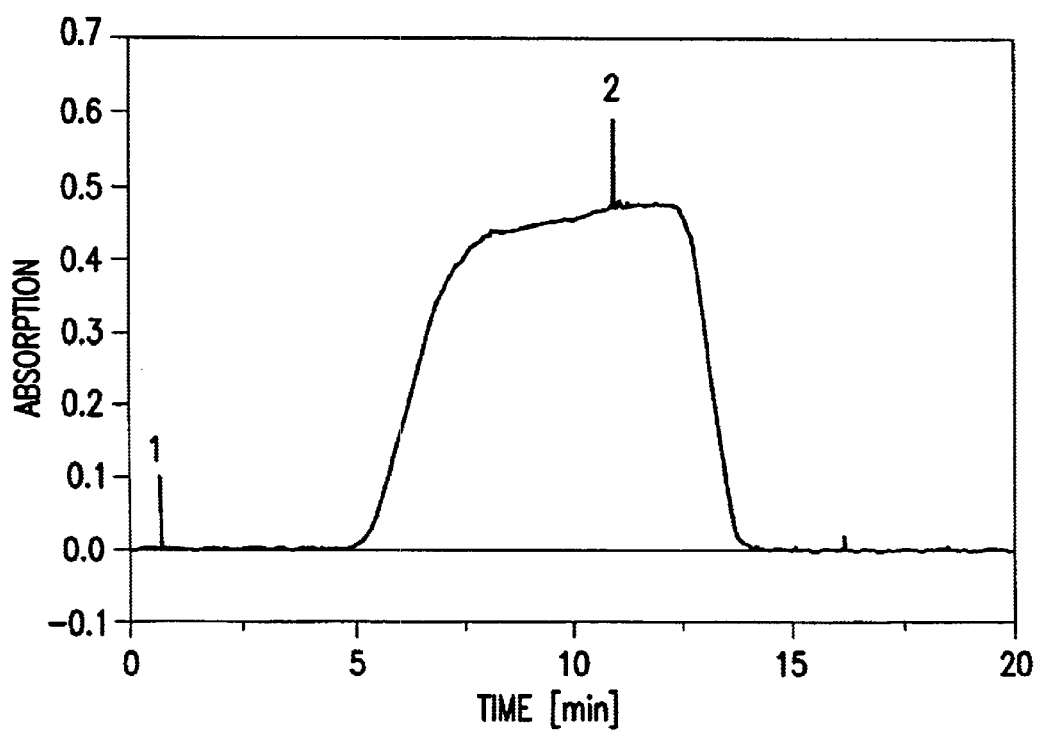

FIG. 5 shows experimental confirmation of the high speed of separation in an example with a hollow fiber that is permeable to the components. A continuous sample stream is conducted through the hollow fiber and detected at the downstream end without the influence of a field (point 1 to 2). After application of the electric field (point 2) the protein is removed entirely from the hollow fiber (reduction in absorption) with a low response time (of the order of a minute) because the pH value of the surrounding solution does not correspond to the IP of the protein.

Figure 6:
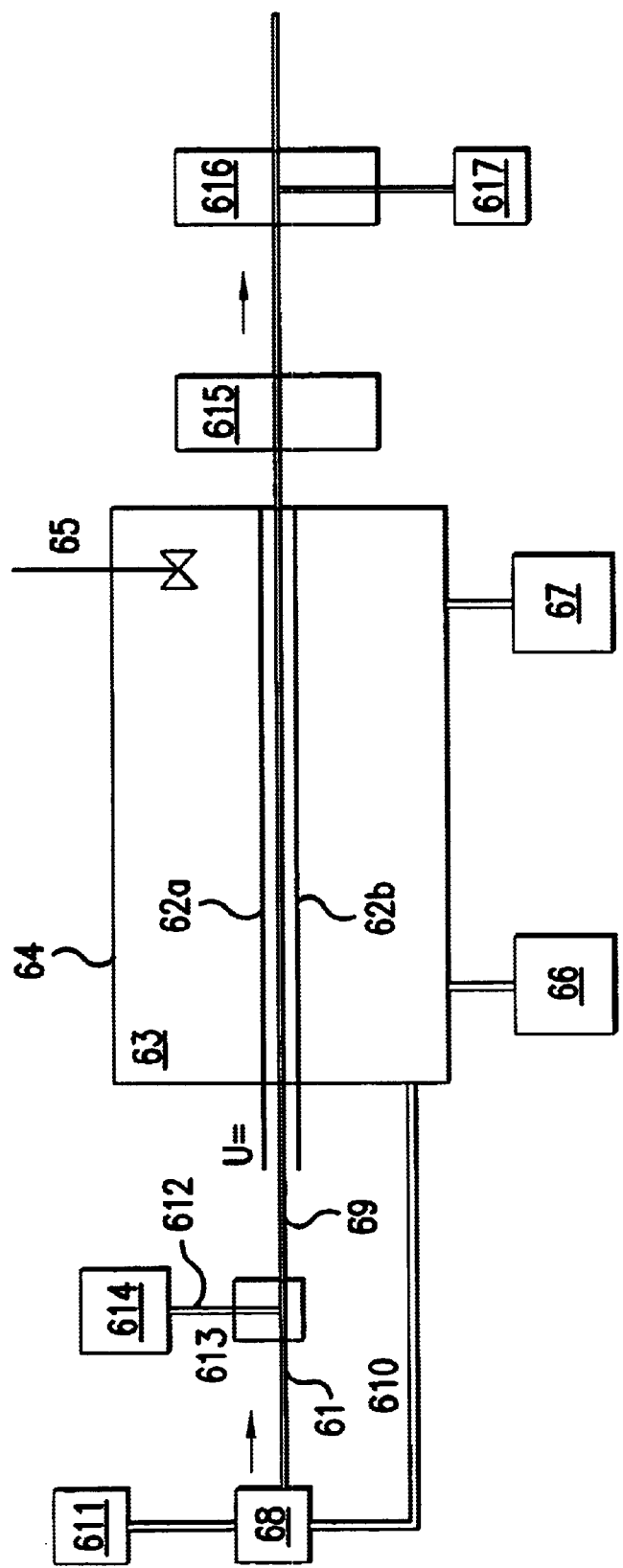

FIG. 6 is a schematic of a separation device according to the invention for separation of ampholytic molecules as a function of IP. The hollow fiber 61 and two electrodes 62a, 62b are arranged in an enclosure 64. The hollow fiber and the electrodes are parallel to one another, the hollow fiber being between the electrodes. The enclosure 64 is filled with the surrounding solution 63 and joined to a reservoir 66. The pH setting device 67 sets the pH value of the surrounding solution. Because of the semi-permeability of the hollow fiber, the pH value of the guiding fluid tracks the pH value of the surrounding solution. At least one stirring means 65 is provided to ensure spatial pH constancy. At the upstream end of the hollow fiber 61 there is a pump 68 to convey the guiding fluid 69. The pump 68 is joined by a connection 610 (eg hose) to the enclosure 64 and/or to a separate fluid reservoir 611. As an alternative to the pump 68 for advancing the guiding fluid, a suction device can be provided at the downstream end of the hollow fiber, thus ensuring the necessary flow of the guiding fluid in the right direction.

Introduction of the sample 612 to the guiding fluid stream as a narrow band is through a three-way injector block 613 fitted with a means of dosing (eg Hamilton injector 614). But microducts can also be provided in the hollow fiber wall for sample introduction.

At the downstream end of the hollow fiber there is a detector unit 615 for identifying the substances in the lumen after passing through the hollow fiber, and a three-way cock 616 for controlled transfer of fluid from the hollow fiber into a fraction collector 617. The detector unit 615 can be configured for opto-spectroscopic measurement for example. If the hollow fiber consists of UV-permeable glass, proteins with absorption in the UV band can be detected direct in the hollow fiber.

Particles with an IP differing from the pH value are fixed on the inner wall of the fiber. Particles with an IP corresponding to the pH value are able to pass through the fiber unhindered. By variation of the pH value during separation it is possible to separate individual fractions, which then are rinsed one after the other from the fiber volume.

The device according to FIG. 6, depending on the form that the hollow fiber takes, can be used as both a separating device and a purifying device for the methods explained above. It is possible to subdivide the reaction cavity so that it will hold several surrounding solutions differing in their pH value. The electrodes are then interrupted and driven separately as appropriate. Several devices as in FIG. 6 can also be cascaded.

In the design of the collection arrangement as a hollow fiber, according to the invention, the guiding fluid possesses a flow cross-section that is much less than the length of the separation path. Thus the electrodes, between which the hollow fiber is located, can be arranged with a small spacing so that small voltages suffice to generate high field strength. Typical separator arrangements can be operated with voltage between 1 and 10 V for example. Such small voltages avoid production of excessive heat and generation of electrolysis products, thus relaxing conditions for samples sensitive to heat. Compared to cIFF technology, which was referred to at the beginning, the invention reduces the gap across which an electric field is applied by about three orders of magnitude.

Further benefits of the invention are the short analysis or separation times (approx. 10 min or less), the possibility of automated and permanent detection in a flow-through system, and the easy handling with conventional, elaborate gel or IPG-IEF techniques. Furthermore, the invention allows separated components to be temporarily retained and released again after a predetermined field or pH alteration.

A further variant of isoelectric separation according to the invention consists in a concentrating procedure. A diluted solution with one or more components flows continuously through the hollow fiber and is exposed to the influence of the field. The non-isoelectric components are fixed spatially on the hollow fiber wall. Following this flow the field is removed and a solution (rinse) flows through the hollow fiber that is lens than the total volume of the previous diluted solution. The rinse detaches the molecules fixed to the wall, which are thus released and leave the fiber, resulting in a solution of greater concentration than the original diluted solution.

Another application is in the acceleration of dialysis processes. If the ionic concentration of the surrounding solution is less than that of the guiding fluid, ions will diffuse from the hollow fiber. This process can be very much accelerated by the electric field.

With the device presented here it is also possible to characterize a substance by its isoelectric parameters. This is of special interest when characterizing isoenzymes.

In what follows, modifications of the device according to FIG. 6 are explained with reference to FIG. 7 through FIG. 12.

Figure 7:
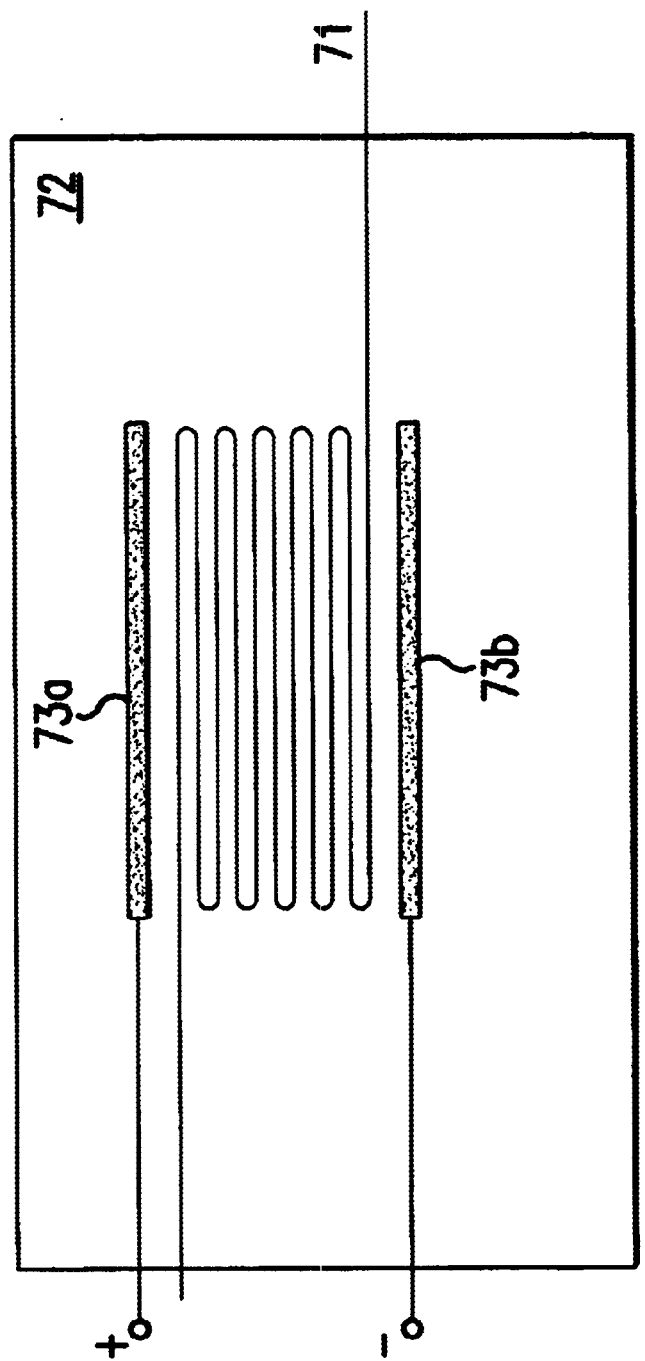

FIG. 7 shows an example of an implementation in which a bent hollow fiber 71 is arranged in the enclosure 72. The hollow fiber has a spiral shape. The electrodes 73a, 73b are matched to the geometry of the hollow fiber. In this example the electrodes 73 are ring electrodes, just covering the spiral cross-section. The spiral shape of the fiber makes it possible to separate larger amounts of sample simultaneously, because a larger amount of sample can be retained in the region of the wall where the flow velocity is zero (see FIG. 1). On a micropreparative scale this also allows continuous introduction of the sample.

Figure 8:
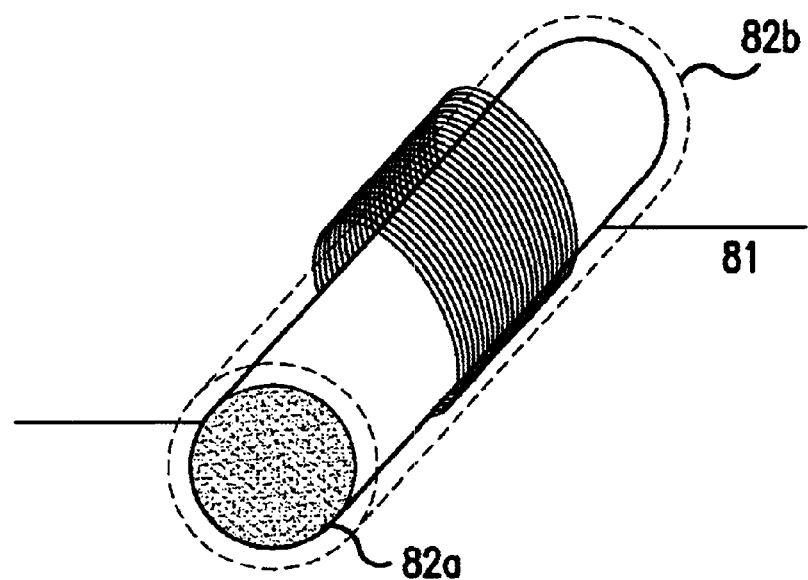

FIG. 8 also shows a spirally shaped hollow fiber 81 wound onto a cylindrically shaped electrode 82a. The counter-electrode 82b (shown dotted) can be pushed over the arrangement as a hollow cylinder for example. The surrounding solution can flow through the gap left between the electrodes. The arrangement according to FIG. 8 is characterized by high charge or separation capacity plus a small space requirement and low voltages.

Figure 9:
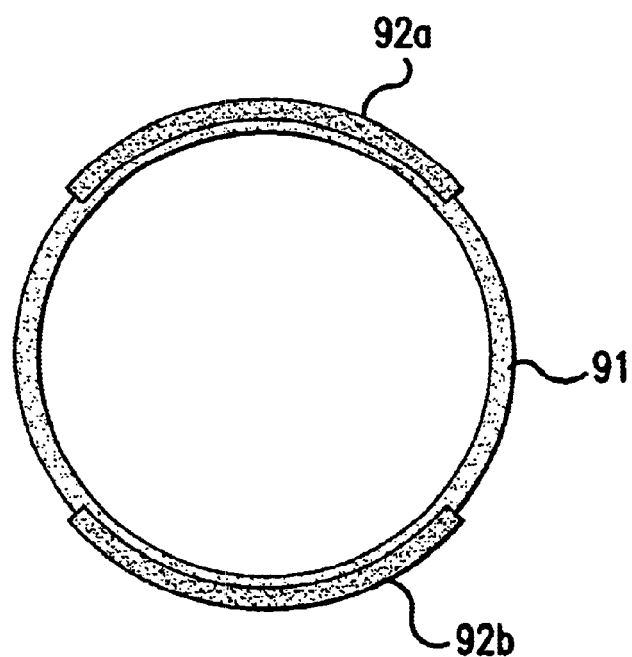

The electrodes and collection means, described up to now as separate components, can also be joined together as in FIG. 9. FIG. 9 shows, the cross-section of a hollow fiber 91 with electrodes 92a, 92b, which are deposited as a thin layer on the outer wall of the hollow fiber. In this way even smaller voltages can be used to produce high field strength. The surrounding solution influences the inside of the hollow fiber through the regions of the hollow fiber that have been left free. However, it is also possible to operate the system according to the invention without a surrounding solution.

Figure 10:
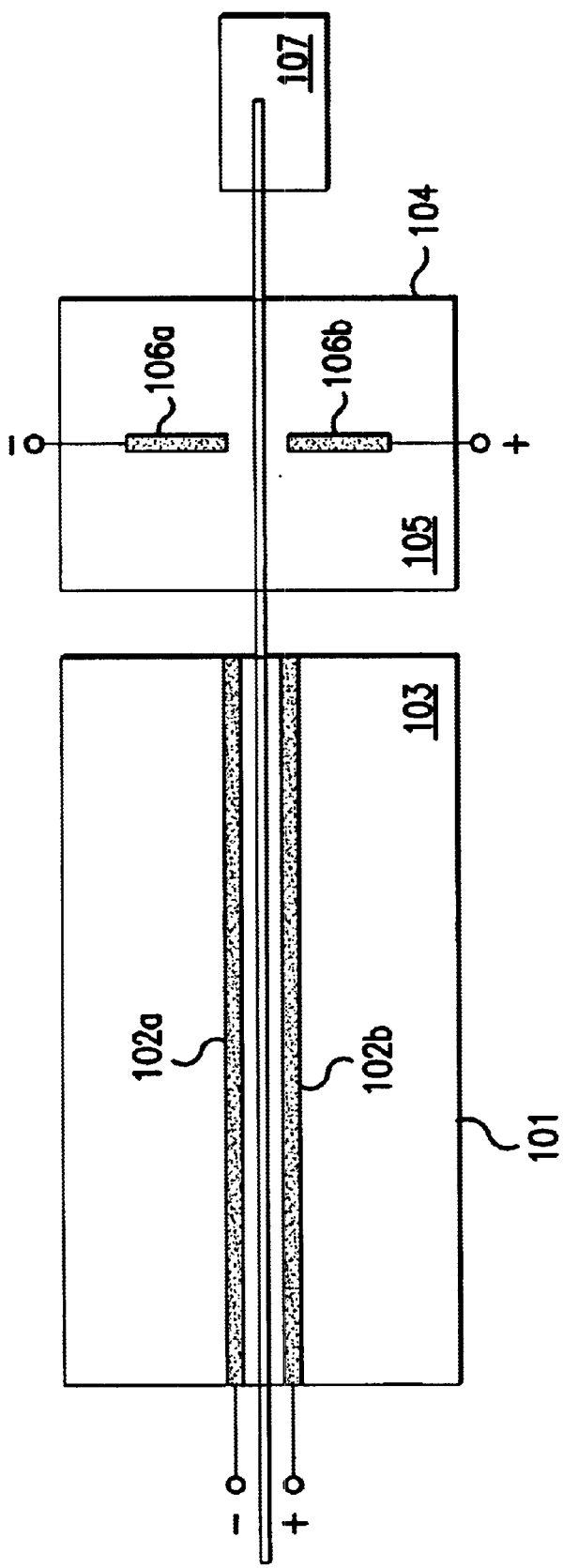

FIG. 10 shows the combination of a separating device (reaction cavity 101 with hollow fiber and electrodes 102a, 102b) with a concentration boosting device 104. This combined arrangement is operated so that, to begin with, there is fractionating of a substance mix according to the invention in the separation region. In the concentration boosting device 104, whose surrounding solution 105 has a different pH value to the surrounding solution 103 in the separation region, the purified fraction can be fixed with the electrodes 106a, 106b as a narrow band and, after removal of the electric field on these electrodes, be applied to the fraction collector 107 as a concentrated fraction.

Figure 11:
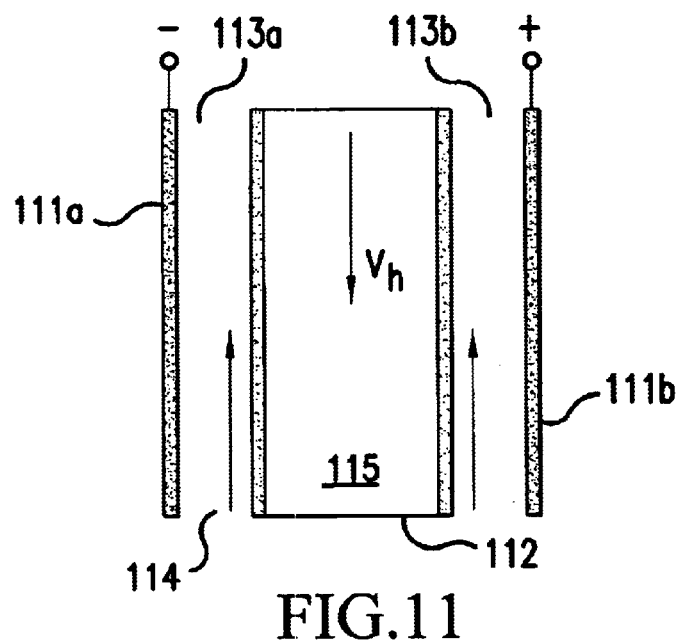

The multi-compartment system according to FIG. 11 implements a counterflow principle where the surrounding solution 114 in the particular reaction cavity is set into flow motion. The direction of flow should be opposite to the direction of flow in the hollow fiber 112. A membrane 113a, 113b is placed between the electrodes and the hollow fiber 112 to intercept any electrolysis products appearing on the electrodes 111a, 111b. The flow of the surrounding solution also serves to stabilize the pH in the reaction cavity.

Figure 12:
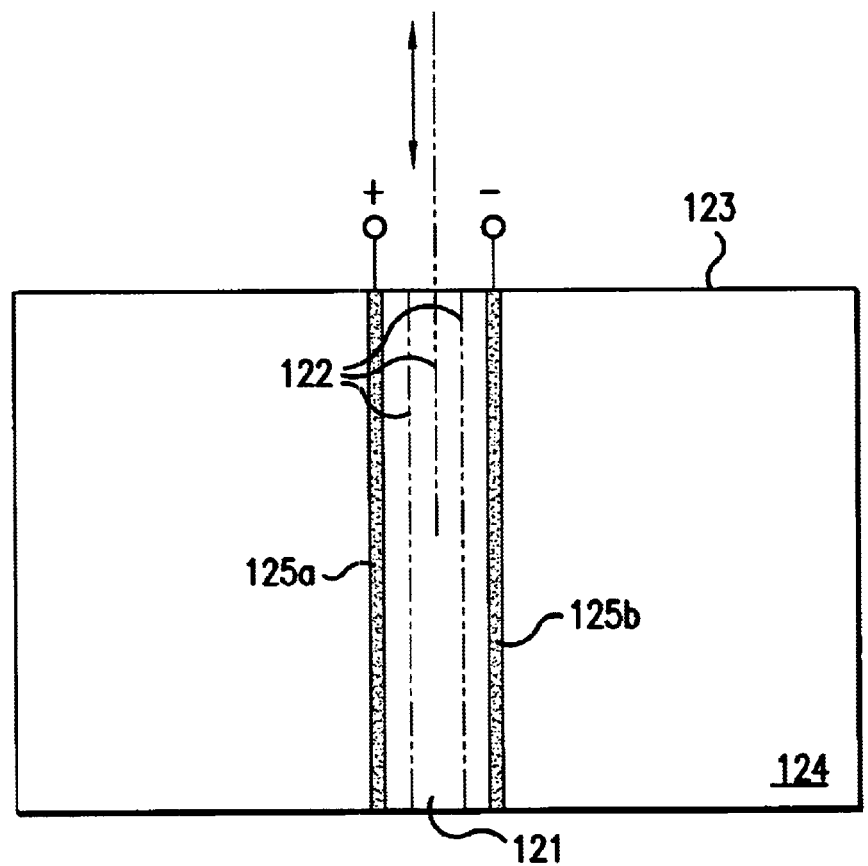

In the invention it is not absolutely necessary for the guiding fluid to flow, it can also be static. It is also possible to move the collection means relative to the guiding fluid. This is illustrated in FIG. 12. A chamber 123 is filled with a protein mix 121 and is demarcated by permeable membranes 122. The chamber 123 is brought into the pH-regulated region 124. When the electric field is applied through electrodes 125a, 125b, single proteins drift, according to the principle of the invention, to the membranes 122. The membranes can be provided with movable, protein-binding intermediary membranes that are withdrawn in the direction of the arrow once they are occupied by the separated proteins. Alternatively it is possible to provide an elution stream in the direction of the arrow to rinse the separated proteins out of the membrane region.

The invention also foresees providing a separating device with several, cascaded collection means or several separation regions arranged in serial or parallel. Instead of the described hollow fiber, the collection means can also be formed of any porous membranes or layers that have appropriate compartments for the guiding fluid, next to which the electrodes are placed.

The semi-permeability of the collection means (eg of the hollow fiber) can vary over their length in the direction of flow so that section by section certain ions of the guiding fluid and/or surrounding solution and/or only certain molecules are allowed to pass.

It is also possible to modify the inner wall of the hollow fiber by chemical or physical methods to alter the effect of the electric field. The inside of the hollow fiber can be filled with gels, microparticle suspensions or granulates, or a gel can be added to the reaction cavity too. The hollow fiber can be wound at a certain spacing round an electrode of any shape and the counter-electrode can be matched to this geometry.

The collection means can be formed of a multi-fiber array consisting of a large number of hollow fibers, through all of which the guiding fluid flows. The flow through the fibers is at different rates, however, so that the efficiency of separation can be influenced as a function of substance.

A DC voltage, an AC voltage or any other programmable voltage can be applied to the (at least two) electrodes so that the field strength in the guiding fluid is varied accordingly. This allows the formation of predetermined separation patterns on the collection means.

The electrodes can have modified surfaces or be of modified materials to reduce any electrolytic reactions that might appear. The electrodes can be porous or of layers (eg gels, spacers).

The collection means can be bordered by flat membranes forming a compartment for the guiding fluid. The compartment can be subdivided with the aid of further membranes to hold different protein fractions. In an arrangement of this kind the sample to be separated can be introduced on a membrane that has absorbed the sample.

A special advantage of the separating device according to the invention lies in miniaturization, in a preferred implementation it is intended to form and drive at least parts of the electrodes with electronic components like transistors or diodes, and to produce the three-dimensional arrangement of the electrodes, ducts, hollow fiber holders and reaction cavity using the technologies of semiconductor structuring.

What is claimed is:

1. A method for isoelectric particle separation, said method comprising the steps of:

providing collection means arranged adjacent to a fluid and adapted for soluble fixing of the particles in the fluid, wherein said collection means comprise at least one semipermeable or porous wall, along which the fluid with the particles to be separated flows with a flow velocity, and wherein electrode means extend, at least in part, along a direction of flow over the length of the semipermeable or porous wall, providing a fluid containing particles that have a net charge or charge density that is a function of the pH value of their surroundings, setting the pH value of the fluid, imparting motion to the particle-containing fluid, generating electric field forces by said electrode means, permitting at least one predetermined particle type to undergo a change in motion as a function of charge through the effect of the electric field forces, permitting the particle type undergoing the change in motion by the electric field forces to move to said collection means, retaining said particle type on the collection means at least temporarily, and reducing or dropping to zero temporarily the flow velocity of the fluid when the particles to be separated are exposed to the electric field forces in order to enhance separation of the particles being separated while the fluid with the particles to be separated flows along the semipermeable or porous wall.

2. The method according to claim 1, wherein the moved particle type comprises particles whose isoelectric point does not correspond to the pH value of the fluid.

3. The method according to claim 1, wherein the particles to be separated comprise ampholytic molecules or other particles, synthetic particles or biological cells, viruses, or other biological objects whose electrical characteristics correspond to the electrical characteristics of ampholytic molecules.

* * * * *